United States Patent [19]

Kibbey et al.

[11] Patent Number: 5,670,054

[45] Date of Patent: Sep. 23, 1997

[54] METHOD AND SYSTEM FOR IDENTIFICATION, PURIFICATION, AND QUANTITATION OF REACTION COMPONENTS

[75] Inventors: Christopher Edmund Kibbey; Gregory Alan Robertson, both of Ann Arbor, Mich.

[73] Assignee: Warner Lambert Company, Ann Arbor, Mich.

[21] Appl. No.: 626,290

[22] Filed: Apr. 4, 1996

[51] Int. Cl.⁶ .................................................. B01D 15/08
[52] U.S. Cl. ...................... 210/656; 210/659; 210/143; 210/198.2
[58] Field of Search .............................. 210/635, 656, 210/659, 143, 198.2; 95/82, 86; 96/101, 104

[56] References Cited

U.S. PATENT DOCUMENTS

| | | | |
|---|---|---|---|
| 3,717,028 | 2/1973 | Annino | 210/656 |
| 4,237,422 | 12/1980 | Lenhardt | 210/656 |
| 4,454,043 | 6/1984 | Ting | 210/659 |
| 4,532,043 | 7/1985 | Prud'homme | 210/656 |
| 4,579,663 | 4/1986 | Poile | 210/656 |
| 4,719,017 | 1/1988 | Uchino | 210/656 |
| 4,762,617 | 8/1988 | Stevens | 210/656 |
| 4,806,250 | 2/1989 | Takata | 210/659 |
| 4,859,342 | 8/1989 | Shirasawa | 210/656 |
| 4,925,567 | 5/1990 | McAleese | 210/656 |
| 4,927,532 | 5/1990 | Pospisil | 210/656 |
| 5,091,092 | 2/1992 | Newhouse | 210/656 |
| 5,107,908 | 4/1992 | Newhouse | 210/656 |
| 5,121,443 | 6/1992 | Tomlinson | 210/656 |
| 5,203,992 | 4/1993 | Drouen | 210/656 |
| 5,209,853 | 5/1993 | Lynch | 210/198.2 |
| 5,277,871 | 1/1994 | Fujii | 210/656 |
| 5,294,336 | 3/1994 | Mizuno | 210/198.2 |
| 5,306,426 | 4/1994 | Afeyan | 210/635 |
| 5,350,520 | 9/1994 | Kikumoto | 210/656 |
| 5,395,521 | 3/1995 | Jagadeeswaran | 210/198.2 |
| 5,436,166 | 7/1995 | Ito | 210/656 |
| 5,443,734 | 8/1995 | Fetner | 210/656 |
| 5,508,204 | 4/1996 | Norman | 210/656 |

OTHER PUBLICATIONS

"The Advantages of Evaporative Light Scattering Detection in Pharmaceutical Analysis by High Performance Liquid Chromatography and Supercritical Fluid Chromatography" Lafosse, et al. *Jour.of High Resolution Chromatography*, vol. 15,pp. 312–318, May 1992.

"Analysis of Steroids in Bulk Pharmaceuticals, etc.", Paul A. Asmus and John B. Landis *Journal of Chromatography*, 316 (1984) pp. 461–472.

"Validation of An EPLC Method for The Determination of Sodium in LY29311 Sodium, etc." Jeffrey A. Peterson and Donald S. Risley, *Journal of Liquid Chromatography*, 18(2) pp. 331–338 (1995).

*Primary Examiner*—Ernest G. Therkorn
*Attorney, Agent, or Firm*—Brooks & Kushman P.C.

[57] ABSTRACT

An automated HPLC system separates, identifies, purifies, and quantitates complex mixtures of reaction products or natural products on a semi-preparative or preparative scale, thus enabling rapid compilation of combinatorial libraries with minimal operator involvement.

15 Claims, 5 Drawing Sheets

METHOD AND SYSTEM FOR IDENTIFICATION, PURIFICATION, AND QUANTITATION OF REACTION COMPONENTS

TECHNICAL FIELD

The present invention pertains to the identification, purification, and quantitation of complex mixtures of chemical reaction products, naturally occurring products, or other complex mixtures of chemicals where the separation of one or more of the components of these mixtures in semi-preparative or preparative quantities is desired. Specifically, the present invention pertains to an automated procedure which enables separation of product compound(s) from mixtures originating from combinatorial library generation, and quantitation of the product compound(s).

BACKGROUND ART

The separation, purification, and identification of reaction products contained in complex organic reaction mixtures or components of naturally occurring biological chemicals or their extracts has long been of immense importance. The painstaking methods of the past have given way to such separation techniques as thin layer chromatography (TLC), gas-liquid chromatography (GC), gel permeation chromatography (GPC), molecular distillation, liquid chromatography (LC), and high performance liquid chromatography (HPLC). These techniques were, for the most part, originally developed as analytical methods for the quantitation of small (µg or µmol) quantities of sample. Many of these techniques now have preparative scale analogs. The advantages and disadvantages of each technique are relatively well known, and will not be set forth herein. Of all these separation techniques, HPLC has proven to be the most powerful, flexible, and useful for the separation of mixtures of small (e.g., <1000 amu) organic molecules. While the fundamental principles governing HPLC are well understood, a brief description of the general technique and its laboratory applicability are merited.

The HPLC column is a hollow, pressure-resistant tube containing an adsorbent (i.e., solid support, or packing). A mobile phase enters the column through standard high pressure fittings, and exits the column through the opposite end. The pressure and volume of the liquid, mobile phase, are maintained by a high pressure pump. In preparative and semi-preparative applications, the HPLC column effluent is generally directed to a detection device prior to being isolated with a fraction collector. In typical operation, a sample containing several components, for example one or more desired reaction products which also may contain various impurities is injected onto the column at a sample injection port. The differential adsorption of products and impurities on the solid stationary phase causes the individual sample components to traverse the length of the column at different linear velocities owing to differences in the amount of time the sample molecules spend in the moving liquid phase versus the amount of time they spend on the stationary solid support. Sample molecules whose affinity for the stationary phase is weak will move rapidly through the column, while those more strongly adsorbed on the solid support will move through the column more slowly. As a result, the various molecular species are efficiently separated. The high separation efficiency inherent in HPLC is due primarily to the use of highly purified solid supports characterized by a narrow distribution of small diameter (<10 µm) spherical or irregular particles efficiently packed within the column. The nature and operation of HPLC columns is well known to those skilled in the art, and commercial systems containing integrated mobile phase pumps are available.

The chromatographic resolution of sample components is optimized through chemical modification of the stationary phase and/or compositional changes to the mobile phase eluent. For example, HPLC separations may be carried out using a constant eluent composition (isocratic elution), or alternatively the composition of the mobile phase may be varied following a preset gradient program. In gradient elution, the solvent composition of the eluent is changed gradually during the separation by proportioning two, three, or more individual solvents or solvent mixtures. These solvents may be combined through the use of separate metering pumps and an appropriate solvent mixing device, or alternatively, the individual solvents may be premixed and delivered to the column via a single high pressure pump. Accurate and precise blending of the individual solvents over the course of the gradient program is achieved through microprocessor control over the solvent metering devices, whose instructions in turn are established by the system operator through the HPLC system software. The ability to change the polarity or other properties (pH, ionic strength, etc.) of the mobile phase, the column temperature, and the column length, etc., together with the ability to tailor the selection of the stationary phase to the class of compounds being investigated have made HPLC a valuable separations technique.

The rapid generation of new drug candidates through automated synthetic organic chemistry techniques has become an important part of the drug discovery process at many pharmaceutical companies. A series of compounds having a common structural feature, but differing in the number and/or nature of peripheral sub-groups attached to the parent structure defines a combinatorial library, and the chemical processes by which these sets of compounds are generated is termed combinatorial chemistry. An example of a combinatorial library of pharmaceutically relevant compounds would be the series of hydantoins, consisting of 3-(4-methylphenyl)-2,4-imidazolidinedione, 3-(4-methylphenyl)-5-methyl-2,4-imidazolidinedione, 3-(4-methylphenyl)-5-(phenylmethyl)-2,4-imidazolidinedione, 3-(1-methylethyl)-5-(phenylmethyl)-2,4-imidazolidinedione, 3-butyl-2,4-imidazolidinedione, 3-butyl-5-methyl-2,4-imidazolidinedione, 3-butyl-5-(phenylmethyl)-2,4-imidazolidinedione, and 3-butyl-5-(1-methylethyl)-2,4-imidazolidinedione. In the present application, however, the term "combinatorial library" is taken more broadly, and encompasses, for example, compounds with a given functional group but attached to divergent substrates (e.g., the various aliphatic and aryl isocyanates).

The efficient purification of combinatorial libraries composed of discrete compounds is problematic even with modern automated methods of separation such as HPLC, both preparative and semi-preparative. The advantages of semi-preparative and preparative HPLC (over other purification techniques such as solid phase extraction and liquid-liquid partitioning) for the purification of combinatorial libraries of discrete components are the greater separation efficiencies and sample handling capabilities of semi-preparative and preparative HPLC and the superior automation capabilities of modern HPLC systems. The primary difficulties in purifying combinatorial libraries using semi-preparative, or preparative HPLC techniques lie in the areas of chemical component selection and identification.

Conventional semi-preparative and preparative HPLC systems do not provide structural information about the components present in a given sample mixture, nor do they provide a means for predicting the elution of a particular component in a sample mixture prior to chromatographic analysis. As a consequence, the purification of combinatorial libraries by semi-preparative, or preparative HPLC usually involves the laborious collection of arbitrarily spaced fractions of the HPLC column effluent, followed by exhaustive analysis of the collected fractions by mass spectrometry or $^1$H-NMR to determine which of the collected fraction(s) contain the desired product component. In addition, the size of the collected fractions must be made small enough to ensure that any closely eluting impurities present in the sample mixture are excluded from the fraction(s) containing the desired product component. Collecting large numbers of fractions per sample becomes problematic for the purification of large compound libraries, because the total number of analyses that must be performed on the collected fractions for the entire library is greatly increased. Further, the potential for sample handling errors in this process increases with the number of fractions collected.

In the pharmaceutical industry, the purified components of combinatorial libraries are subjected to testing for biological activity in high-throughput screening assays. In order to gain quantitative information regarding a compound's biological activity, it is necessary to determine the concentration of the compound in the solution submitted for testing. Quantitation of combinatorial libraries of pharmaceutical interest by conventional HPLC methods is nearly impossible to perform without well characterized reference standards, and this is a direct consequence of the development of HPLC instrumentation and methodologies within a paradigm that has focused on single component analyses. For example, modern HPLC systems employing UV detection are well suited to the quantitation of a single analyte or set of analytes present in an array of multi-component sample mixtures suspected to contain the analyte(s). These systems, however, are not amenable to quantitation of samples sets in which the composition of each sample within the set is chemically unique and where appropriate reference standards for each sample component are unavailable, the latter being descriptive of combinatorial libraries.

There are a number of commercially available detectors compatible with HPLC, including flame ionization detectors, refractive index detectors, fluorescence detectors, and UV, visible and IR detectors. These detectors rely upon a specific physical or chemical property of the eluting compound(s) of interest as the basis for signal transduction. Because different chemical compounds within the same structural class can exhibit widely different physical and chemical properties, the use of appropriate reference standards for quantitation is often necessary. As an example, the differences in response factors at 205 nm (see Table 1) for the series of hydantoins previously described are large enough to prevent accurate quantitation with a single hydantoin standard by HPLC with low wavelength UV detection. Quantitation of combinatorial libraries (e.g., the hydantoins) based on a single external standard could be performed using an HPLC detector whose response was proportional to the amount of sample making up the component peak eluting from the column.

TABLE 1

Response Factors (Relative to 5-phenylhydantoin) for a Series of Eight Hydantoins at 205 nm

| | |
|---|---|
| 3-(4-methylphenyl)-2,4-imidazolidinedione | 1.12 |
| 3-(4-methylphenyl)-5-methyl-2,4-imidazolidinedione | 1.09 |
| 3-(4-methylphenyl)-5-(phenylmethyl)-2,4-imidazolidinedione | 1.18 |
| 3-(1-methylethyl)-5-(phenylmethyl)-2,4-imidazolidinedione | 0.93 |
| 3-butyl-2,4-imidazolidinedione | 0.41 |
| 3-butyl-5-methyl-2,4-imidazolidinedione | 0.33 |
| 3-butyl-5-(phenylmethyl)-2,4-imidazolidinedione | 0.72 |
| 3-butyl-5-(1-methylethyl)-2,4-imidazolidinedione | 0.26 |

While there are several mass-sensitive detectors compatible with HPLC, (e.g., refractive index, flame ionization, etc.) they are not practical for use in the rapid quantitation of combinatorial libraries. For example, refractive index detection is incompatible with gradient elution in HPLC and flame ionization detectors require the use of cumbersome interfaces that can be difficult to maintain. Evaporative light scattering detectors (ELSD), commercialized within the last ten years, traditionally have been used to detect and quantitate compounds that absorb poorly in the UV (e.g., phospholipids, alkyl surfactants, lipids, etc.). The use of evaporative light scattering detection for the analysis of combinatorial libraries by HPLC has been reported. The ELSD measures the intensity of scattered light generated by a desolvated, nebulized band of solute particulates passing through the beam of a fixed light source. In general, the response of the ELSD is proportional to the mass of the component eluting from the column. Evaporative light scattering detectors are compatible with high throughput gradient HPLC methods. Unlike other mass-sensitive detectors (e.g., refractive index, etc.) the response of the ELSD is logarithmic rather than linear.

The differences in response between ELSD and UV are illustrated in chromatograms A and B, respectively, of FIG. 1 for the separation of four steroids. Each chromatogram corresponds to the injection of 3.60 µg of pregnenolone, 3.07 µg of estrone, 3.12 µg of cortisone, and 3.06 µg of prednisone as a single solution in the HPLC mobile phase. The elution order of the four steroids in each chromatogram follows: pregnenolone<estrone<cortisone<prednisone. The chromatogram recorded with ELSD shows nearly equivalent peak area response per mass of steroid injected. Further, chromatogram A of FIG. 1 suggests that accurate quantitation of any three of the steroids present in the injected sample could be performed based on the standard peak response of the fourth. By contrast, pregnenolone is not observed in the chromatogram of the sample mixture monitored by UV at 260 nm. The other three steroids give peak area responses that reflect differences in their molar absorptivities at the detection wavelength, rather than the true mass composition of the sample mixture. Efficient quantitation of combinatorial libraries based on the use of a single reference standard is possible by HPLC with ELSD, whereas it would not be possible by HPLC employing more conventional detection methods, such as UV.

Current HPLC technology does not offer a unified workable solution to the task of purifying and quantitating combinatorial libraries. It would be desirable to provide a rapid, efficient and integrated process for the separation, identification, purification, and quantitation of the products of combinatorial chemistry. The ideal process would allow the identification of the desired product in the impure sample mixture to be verified prior to semi- or preparative purification, so that only those sample mixtures containing the desired product components are purified. The purification step would be designed such that it made appropriate use of information gathered on the sample in the identification process, so that fraction collection is minimized and fraction combining steps are eliminated. In addition, the purification process would employ technology compatible with high resolution separations of tens of milligram quantities of sample. The ideal system would be designed such that the major equipment pieces could be used for preparative, semi-preparative, or analytical scale separations. Finally, the system would provide an efficient means for quantitating the product components generated during the purification process. While combinatorial libraries of pharmaceutical interest have served as the primary example for the need for an automated system for purification and analysis of sets of sample mixtures, the automated purification and analysis of other types of samples can be envisioned. Indeed, any purification technique which combines semi-preparative or preparative HPLC with fraction collection could benefit from the features of the automated purification and analysis system described. Such a system would have broad applicability not only to the pharmaceutical industry in its search for new drug candidates, but also to other industries such as the agrochemical industry, to aid in the development of pesticides and herbicides with novel activity, and to the flavors and fragrances industry, to aid in the development of new products.

SUMMARY OF THE INVENTION

The present invention pertains to an automated method of sample identification, purification and quantitation wherein a first HPLC column with defined operating parameters is used to separate a small portion of an impure mixture into its constituent components; the individual components corresponding to the eluting zones of the separated mixture are characterized by mass spectrometry; the chromatographic and mass spectroscopic data generated are stored in digital format, for example one compatible with commercial chromatography software, and the data is used to guide the purification of the remaining sample; the remaining sample is injected on a semi-preparative, or preparative HPLC column; an analog detector output of the semi-preparative, or preparative HPLC system is digitized and evaluated electronically with the previously generated chromatographic and mass spectroscopic data; when elution of a sample component peak corresponding to a desired product peak is sensed, a mechanically actuated, liquid switching value (i.e., a pneumatic or electronic switching valve) is actuated to divert the column eluate from waste to a fraction collection device; and when the end of product peak elution is sensed, the switching valve is actuated to divert the column eluate back to waste collection.

The system disclosed enables rapid purification of samples in quantities useful for pharmaceutical screening while involving minimal operator input and minimum fraction collection equipment. The samples can be readily quantitated with limited additional sample manipulation.

DESCRIPTION OF THE PREFERRED EMBODIMENTS

Figure 1A:
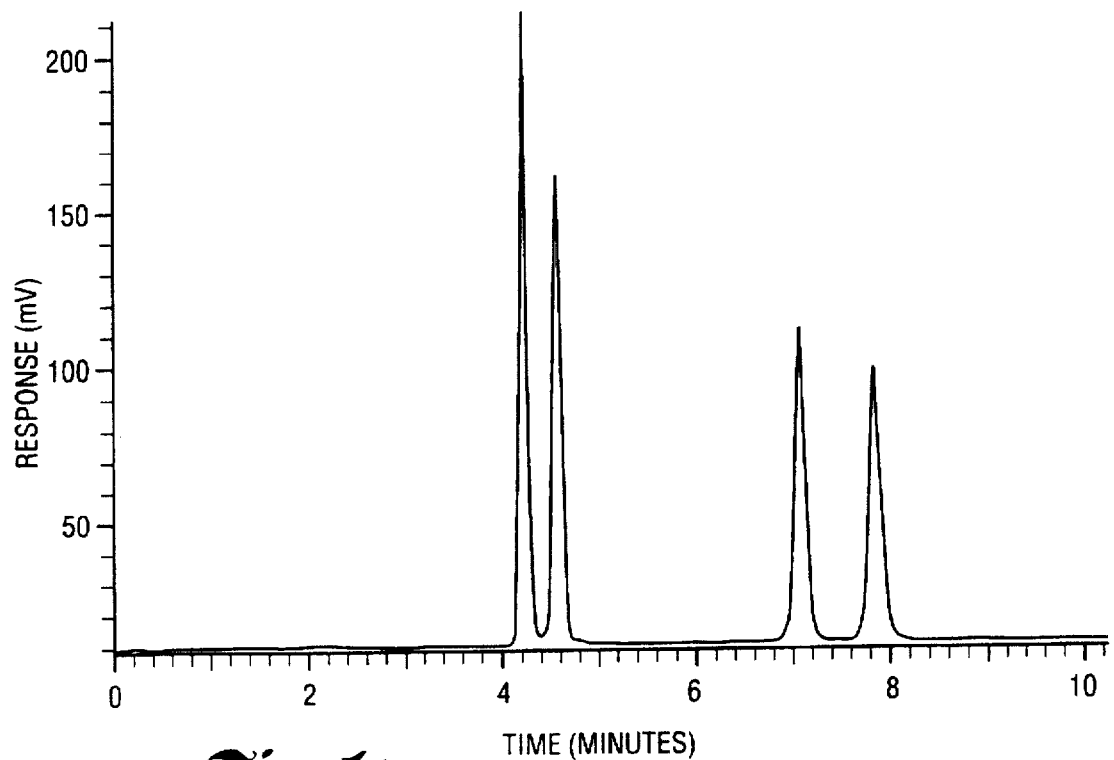
FIGS. 1a and 1b illustrate chromatograms of the separation of a mixture of four steroids by HPLC with ELSD and UV detection, respectively.
Figure 1B:
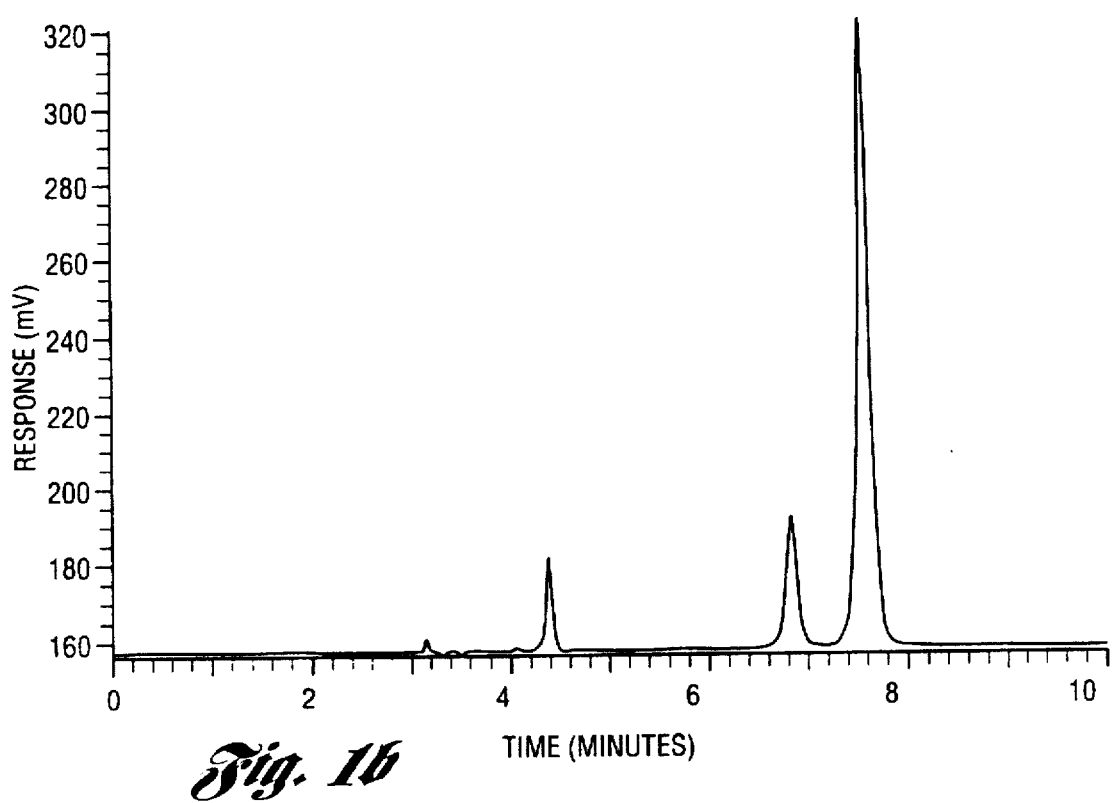
Figure 2A:
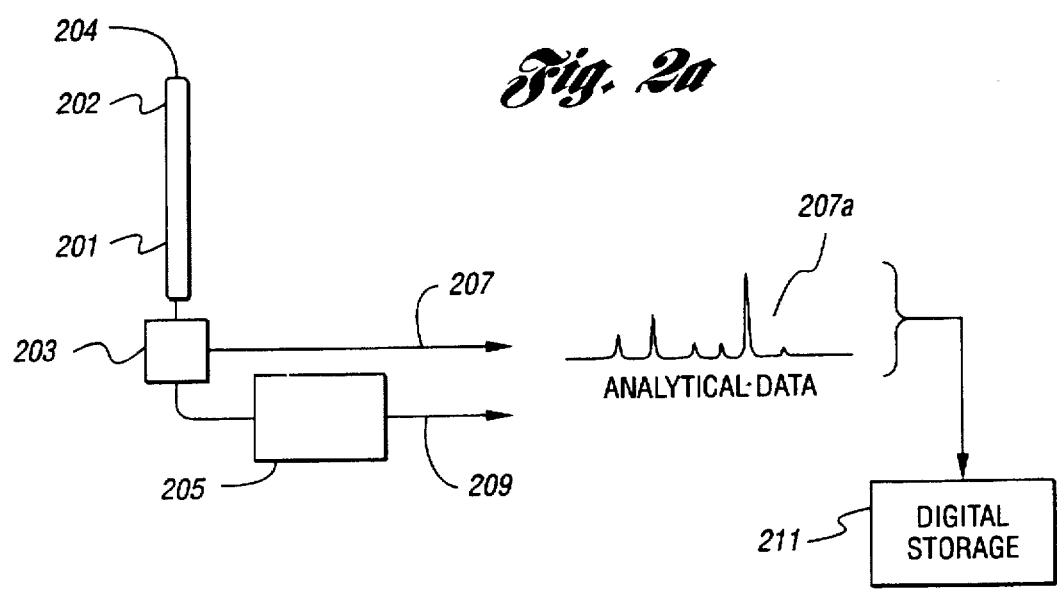
FIG. 2a illustrates a simplified schematic of the identification portion of one embodiment of a HPLC system of the present invention.

The overall operation of the system may be described with reference to FIGS. 2a, 2b, 3a–3c, and 4. In FIG. 2a, a sample to be analyzed is injected onto an HPLC column (e.g., analytical, narrow-bore, or micro-bore) 201 at 202. Pump or pumps supply mobile phase fluid isocratically or by gradient to the column through inlet 204. Eluate from the column is directed to detector 203 which may be of the UV absorbance type or other type. The electrical output 207 from the detector is recorded in standard digital format at 211 by software typically supplied by the analytical HPLC vendor. Examples of such software include PC-1000 software supplied by Thermo Separation Products, PE-Nelson Turbochrom, HP Chemstation, etc. A chromatogram corresponding to the data is illustrated at 207a. All or a portion of the eluate from column 201 is also fed to product identifier 205, which is preferably a closely coupled mass spectrometer. The mass spectrometer output 209 is also stored digitally at 211, and used to identify which peaks are product peaks and which are due to impurities, etc. It is preferable, but not necessary that the chromatographic data file be encoded with the information contained in the mass spectrometer data file prior to further use in the system. The preliminary sample chromatographic data obtained in this step of the process will be referred to herein as the "scout" chromatogram.

Figure 2B:
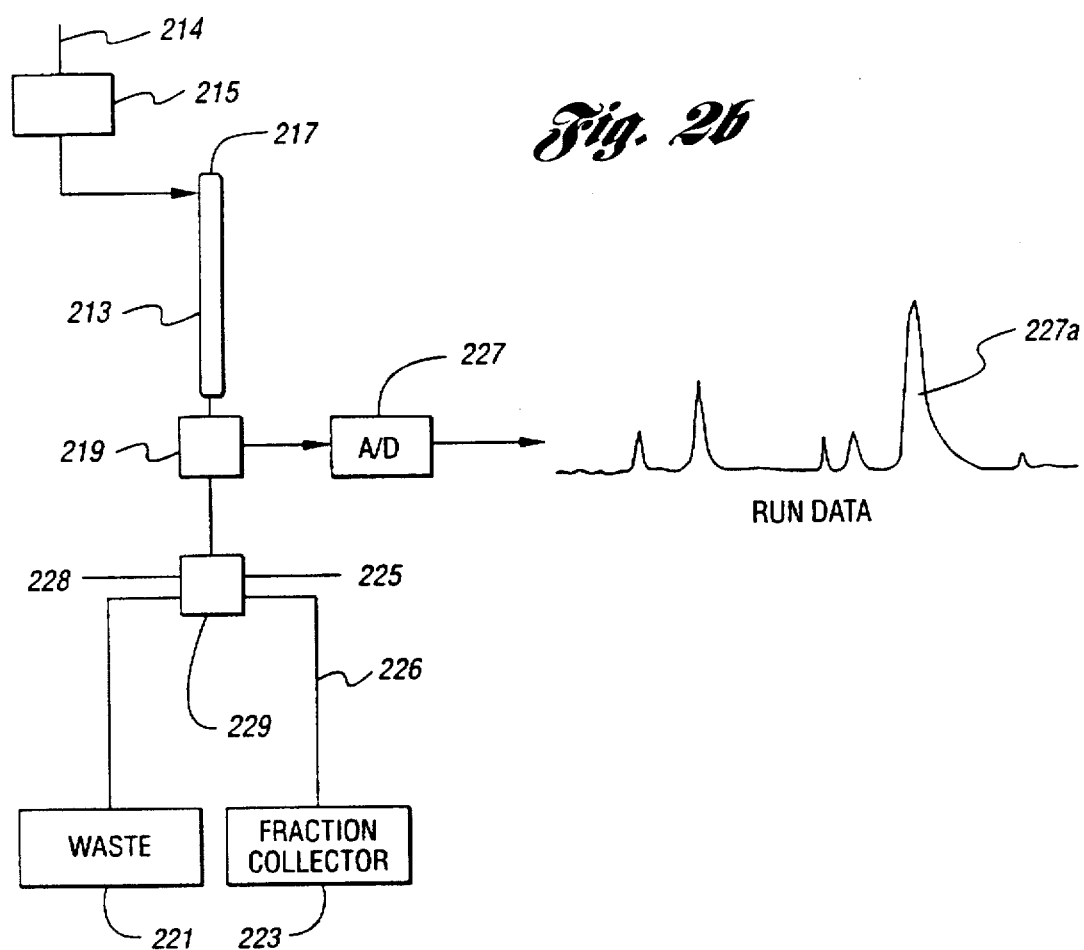
FIG. 2b illustrates a simplified schematic of the purification portion of one embodiment of a HPLC system of the present invention.
Figure 4:
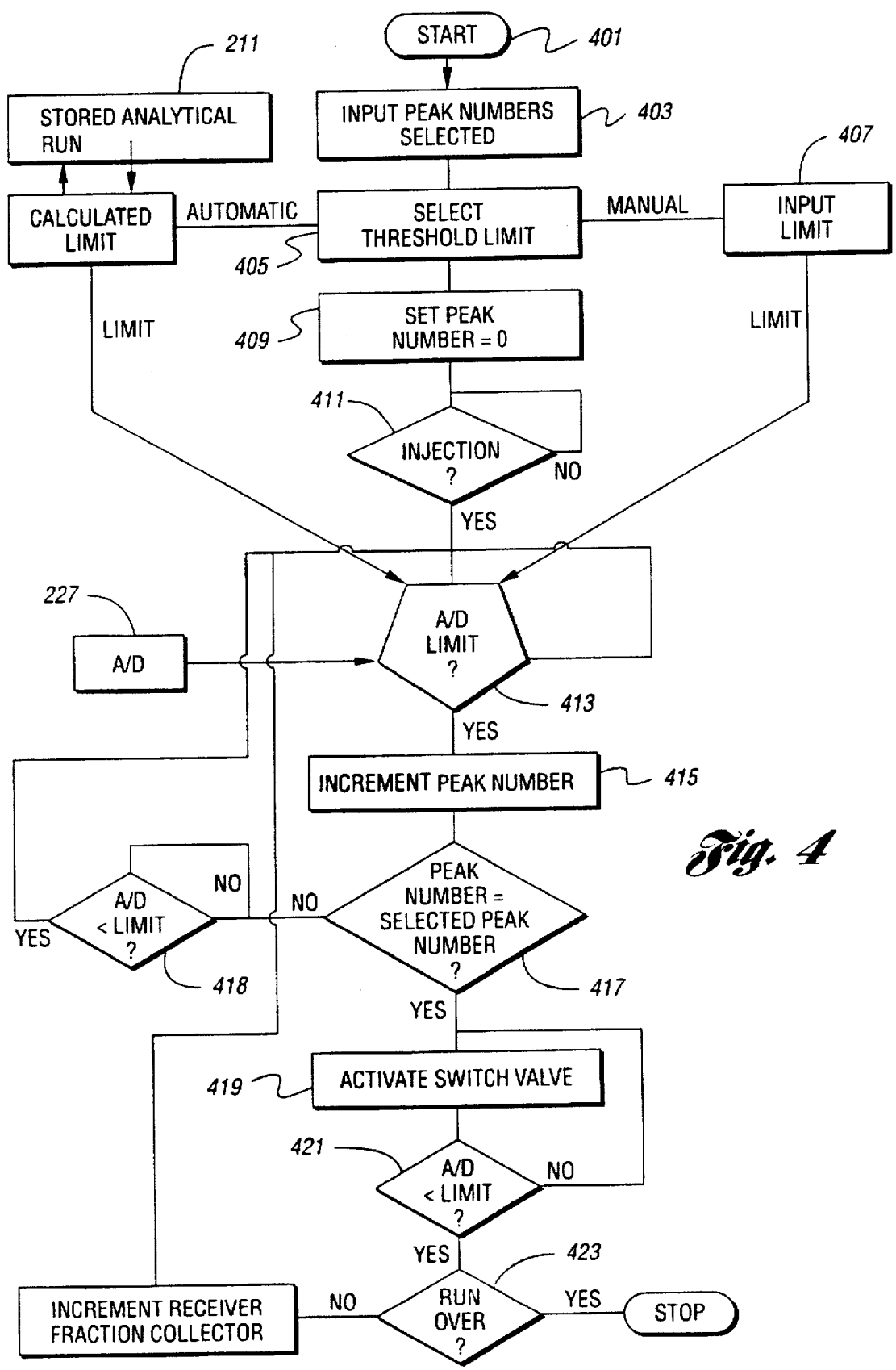
FIG. 4 illustrates a flow chart corresponding to one embodiment of the subject application.

The digitally stored scout chromatogram and mass spectrometric data will be used as per the flow chart in FIG. 4 to guide sample purification on the semi-preparative, or preparative HPLC system, illustrated in FIG. 2b. In FIG. 2b, a larger diameter column 213, than that (201) used in the identification system of FIG. 2a, is used to enable purification of experimentally useful quantities of products. Sample injector 215 is interfaced with a control computer through data line 214. The computer may initiate injection or may receive a signal indicating that injection has occurred. The HPLC system then initiates the mobile phase flow program previously defined by the system operator using the HPLC system pump(s) through mobile phase supply line 217. The solid adsorbent (stationary phase) and mobile phase program are selected such that a similar chromatographic separation to that obtained in the initial analysis (FIG. 2a) of the sample is achieved. In general, the stationary and mobile phase composition and flow program (isocratic, gradient, etc.) will be identical in the two systems described in FIGS. 2a and 2b. However, experience may dictate use of mobile phases of different composition or use of alternate gradients, temperatures, pressures, etc. to partially compensate for differences in chromatographic performance caused by differences in the physical dimensions, or chemical characteristics of the respective columns employed.

The eluate from column 213 or a portion thereof flows through detector 219 whose electrical signal is digitized by analog/digital converter 227. The digitized output may be used in real time without long term storage in memory, but is preferably stored in standard format in addition to being used to compare peak numbers with the stored scout chromatogram derived from the analytical column, as will be described more fully with respect to FIG. 4. From the detector, the eluate flows to electrically switched valve 229 which may have several alternative outlets as well as an alternative inlet 225 which may be used to supply fluid to flush the collection line 226. During most of the purification run, switching valve 229 will be in a position such that eluate is directed to a waste receptacle 221, which may be an actual container mounted on a fraction collector or simply a waste line leading to a large collection vessel.

When switching valve 229 receives a signal through communication line 228 that an identified and desired product peak is eluting, the valve switches from waste collection to fraction collection. The fraction collection vessel 223 may be a single vessel or may be a plurality of collection tubes or vials on an automated fraction collector, the number of which depends upon the volume of the peak being eluted. It is preferable that a single vessel be used for each product collected. When the fraction collection device consists of a plurality of collection vessels, the system software will control the positioning of the column effluent line over the appropriate collection vessel.

Following the sensing of the end of product peak elution, the switching valve switches back to the waste position. For periods of completely unattended operation and/or when more than one product fraction is to be collected, the product collection line 226 will be flushed with mobile phase or with wash solvent supplied through line 225. If more than one product peak is to be collected from a single run, the automated fraction collector is controlled by the computer (see FIG. 3) to assure that a fresh collection vessel is available. Often, the foregoing procedures will be repeated a number of times in order that purified samples of sufficient size may be obtained.

Figure 3A:
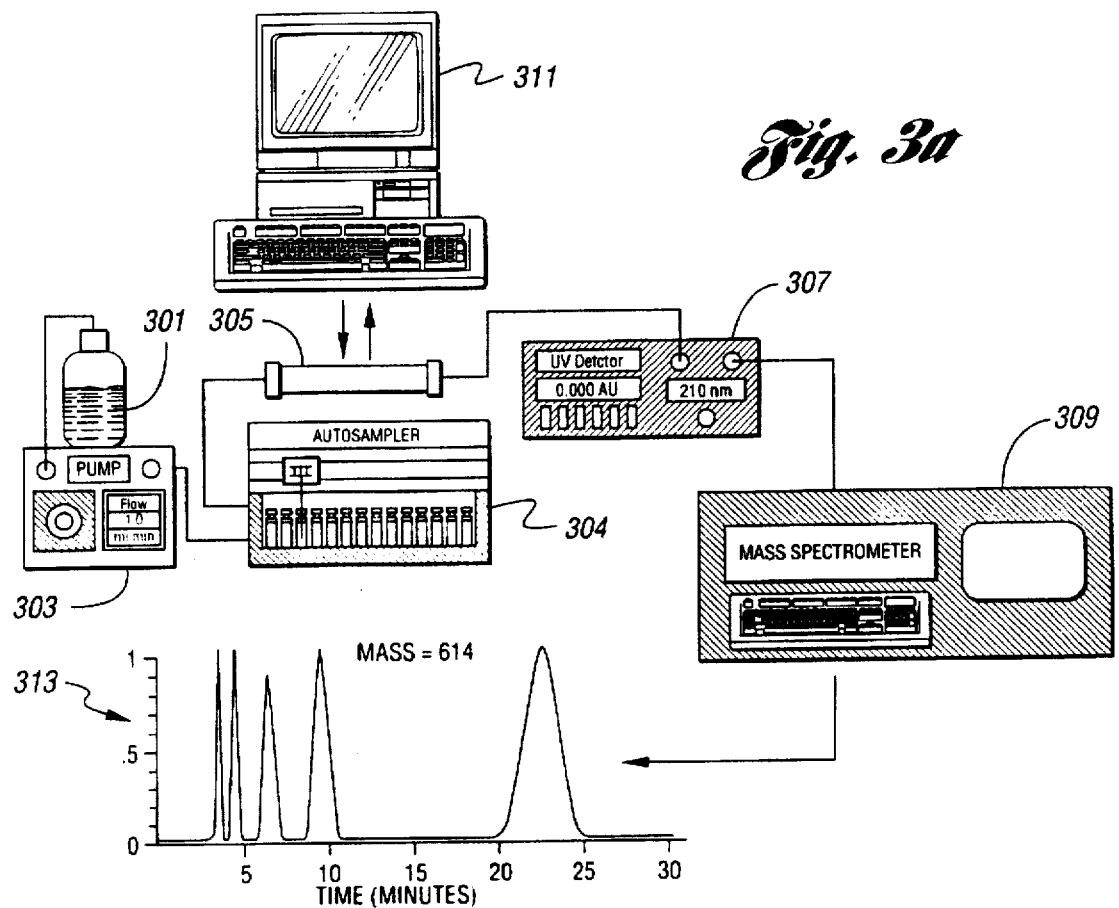
FIG. 3a is a pictorial representation of FIG. 2A.
Figure 3B:
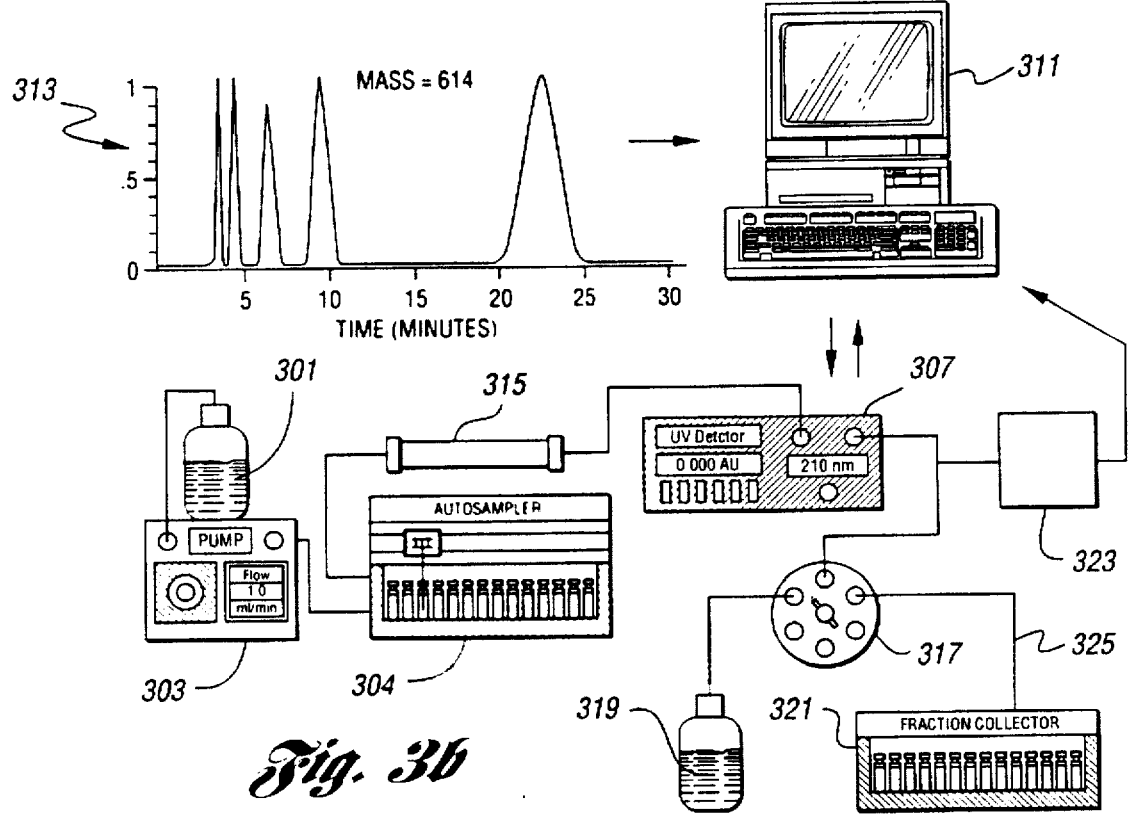
FIG. 3b is a pictorial representation of FIG. 2B.
Figure 3C:
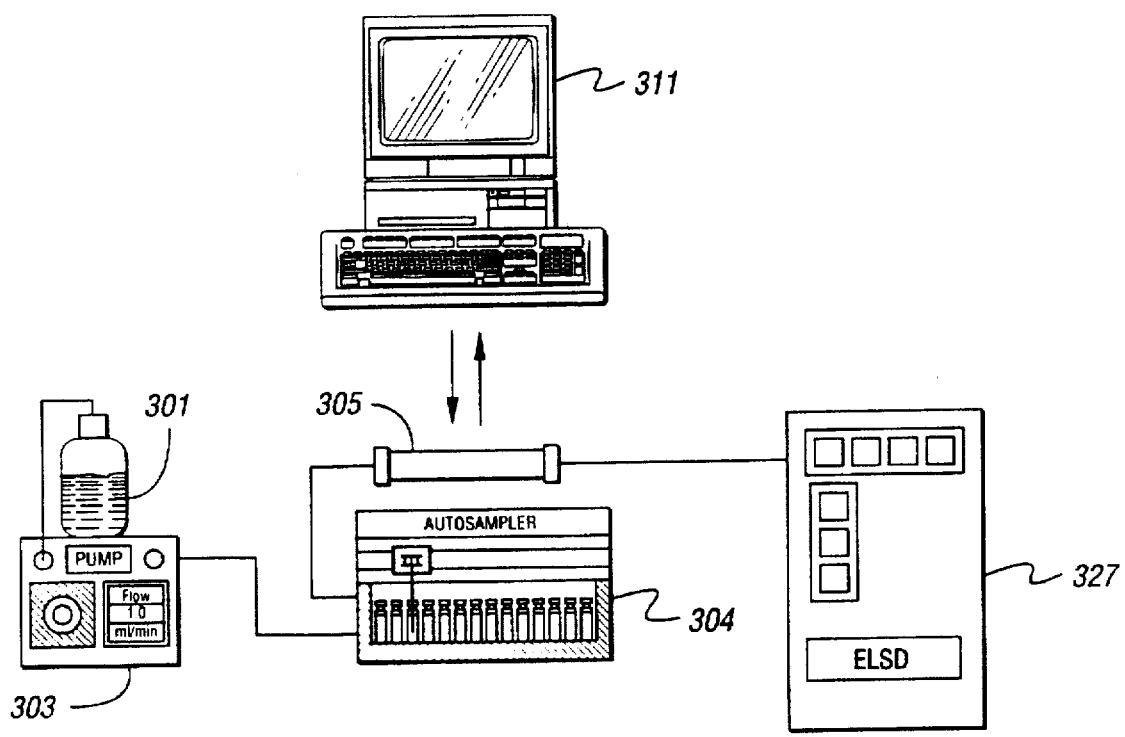
FIG. 3c is a pictorial representation of a simplified schematic of a quantitation portion of one embodiment of a HPLC system of the present invention.

The schematics of FIGS. 2a and 2b and the quantitation step of the instant process are portrayed pictorially in FIGS. 3a–3c. In FIG. 3a, 301 is the mobile phase supply, 303 the HPLC pump/control unit; 304 an autosampler; 305 an analytical HPLC column; 307 a UV detector, the fluid outlet of which is coupled to a mass spectrometer 309. The HPLC system, autosampler, and particularly the UV detector and mass spectrometer are interfaced with computer 311 which digitally stores chromatogram 313 having the peak of interest identified by an associated molecular weight generated by the mass spectrometer.

FIG. 3b illustrates pictorially the purification step, components similar to those of FIG. 3a being numbered similarly. At 315, the HPLC column is a preparative HPLC column, and the eluate, after passing in whole or in part through UV detector 307 is directed by mechanically actuated fluid switching value 317 into waste reservoir 319 or into a compound reservoir in fraction collector 321. The position of switching valve is determined by computer 311 which compares a digital signal from the UV detector created by analog to digital converter 323, to a digital threshold supplied by the user, or generated by computer 311. The position of the delivery tube 325 over the fraction collector is also controlled by computer 311.

In FIG. 3c, the compound reservoirs are mounted in the autosampler 304 and samples injected into analytical column 305, the eluate of which is directed to detector 327, a mass related detector, in this case an ELSD unit. The concentration of sample determined by comparing the ELSD output to one or more standards typical of the combinatorial library of concern, is stored in computer 311 and associated internally with the identity of the sample.

The hardware necessary to implement the system elements shown in FIGS. 2a and 2b and FIGS. 3a–3c are commercially available. For example, a PC-controlled autosampler which can repeatedly inject samples for separation or select different samples for injection is available from Thermo Separation Products as the AS 3000 autosampler. The same company also markets compatible pumps such as the P4000 Quaternary Gradient Pump capable of isocratic elution or programmable gradient elution with up to four solvents; the P2000 binary gradient pump for use with two solvents, and several isocratic pumps. Automated fraction collectors suitable for PC control include the Foxy 200 X-Y Fraction Collectors available from ISCO Corporation. Analog/digital conversion of the preparative HPLC detector output may be achieved using a B&B Electronics Data Acquisition Module Model 2325DA12, which includes 11 channels of 12 bit analog/digital conversion, 3 digital inputs, 3 digital outputs, and contains RS-232 serial port communications. Other hardware is suitable as well.

FIG. 4 is a flow chart illustrating the decision making steps involved in the present invention. Prior to utilization of the purification system, one embodiment of which is shown in FIG. 2b, a sample mixture for which separation, identification, purification, and quantitation is desired will have been separated, the desired component peaks identified, and the scout chromatogram stored in digital format using appropriate standard software, as shown in FIG. 2a at 211. From the start, 401, the user establishes at 403 the spatial positions of the desired peaks to be collected from the chromatogram either numerically from keyboard input, or graphically using a mouse, touchpad, or other device. For example, a single peak, e.g., peak number 3, the third peak in the chromatogram, might be selected, or a plurality of peaks, e.g., peaks 3 and 7 might be selected.

The user next, at 405, establishes a threshold above which the software will recognize the digitized signal from the preparative HPLC column (227, FIG. 2b) as the onset of a peak. The user may input the desired threshold manually at 407, or may choose that the software calculate a suitable threshold based on information previously input to the software, such as the expected noise level of the current column/detector, and information from the scout chromatogram 207a. Also, the run time for the chromatographic purification is specified by the system operator at this point. The peak number counter is set to 0 at 409, and the system idles until sample injection is detected at 411, this point determined by a signal provided by the HPLC system. The switching valve (229 in FIG. 2b) is set such that the column effluent is sent to waste, and the fraction collector is positioned over the tube corresponding to the first component peak to be collected from the sample mixture. Once injection is detected, the digitized detector output from the A/D converter (227, FIG. 2b) is continually compared against the threshold limit at 413. If higher than the threshold, then a peak is being eluted, and the peak number counter is incremented at 415, and compared at 417 with the desired peak numbers input at the start. If not the same, then the A/D output is monitored until it falls below the threshold limit, indicating the end of elution of the non-desired peak at 418.

If the peak counter and desired number are the same, then the switching valve is actuated, switching (FIG. 2b) eluate from waste reservoir 221 to sample reservoir 223. The A/D output is continually compared to the threshold limit at 421 while the switch valve is actuated. When the A/D signal falls below the threshold indicating the end of the peak, the software queries at 423 whether the run is over (based on the previously input values such as total number of peaks to be detected, time limit, mobile phase volume, etc.) If the run has not ended, the receiver fraction collector is incremented so as to position a new receiver for product collection in place of the previous one, and the system returns to monitoring the A/D output/threshold limit at 413. If the run has ended, then the fraction collector arm is moved to the waste position and the fluid transfer line flushed with a designated solvent.

The above flow diagram is simplified, but is representative of the type of decision making steps involved. The actual software implementation is within the skill of the art, and is dependent on such factors as the particular computer or computers used, the operating systems, the vendor-supplied or other HPLC software, and the like. Likewise, the connections between the computer and the preparative HPLC need not be hard wired. It is possible to use infrared or other electromagnetic radiation to relay the control functions to the preparative HPLC, with appropriate modulators/demodulators of common design. Preferably, a single computer, for example an IBM-PC or IBM-PC compatible computer running a multi-tasking operating system such as OS/2 Warp, a product of IBM Corporation, Windows-95, or Windows-NT, both products of Microsoft Corporation, are used. However, there is no reason why the system cannot be implemented on other computers with other operating systems, such as a Macintosh computer running Mac OS or SYSTEM 7™ operating software, both of the latter products of Apple Computer, Inc., or higher end computers available from Digital Equipment Corporation, Hewlett-Packard Corporation, etc. Preferably, the software will be implemented to provide user-friendly screens to assist in inputting the needed information.

The software preferably performs the following functions, at minimum: provides control over switching valve and fraction collector equipment and software setup through appropriate user interfaces (menus, buttons, etc.); allows analytical LC/MS chromatograms to be imported; processes chromatographic data to determine which peak in the scout chromatogram is the product peak to be collected, and determines appropriate threshold level, baseline and slope parameters; displays LC/MS chromatograms during operation; collects the output of UV detector in digital form during operation; decides if product is eluating; controls the switching valve (collect from column or divert stream to waste); controls the fraction collector (move arm to appropriate tube number or waste); and provides iterative cycling to process multiple samples in sequence.

A useful system currently comprises a Thermo Separation Products HPLC system consisting of a Model P-2000 pump, Model AS-3000 autosampler, Model UV-1000 detector, and SN-4000J interface, operating under the vendor's PC-1000 software, within the OS/2 Warp operating system. The customized program to implement the required peripheral control functions (e.g., valve switching, fraction collector operation, etc.) may be written in any programming language or preferably, with the aid of graphical software development tools such as VisProRexx, a product of Hock Ware Inc.

In order to maximize component purity, and to minimize downtime between purification of different samples, it is preferable that the system flush the product collection line (226 in FIG. 2) with an appropriate solvent to remove all traces of the eluted component. This flushing may be accomplished by using the mobile phase being eluted; by using fresh mobile phase, or by using a separately supplied solvent. The switching valve may be designed such that a separate valve connects a supply of fresh mobile phase or solvent to the fraction collector line after the receiving vessel has been changed (to avoid dilution of the desired component), or may use the same valve, shutting off eluate flow until the receiving vessel is changed, then resuming flow through the fraction collection line to flush the latter with mobile phase eluate. Alternatively, the two position switching valve may be replaced by a multi-port switching valve and a bundle of fluid transfer tubes leading to the fraction collector arm. In the aforementioned configuration, the position of the multi-port valve would be incremented stepwise in synchronization with the collection of multiple component peaks from a sample mixture. The use of a bundle of fluid transfer tubes rather than a single transfer tube would reduce the potential for sample cross contamination by allowing the component peaks to be delivered to individual sample collection tubes from separate transfer lines. Following flushing, eluate flow is again to waste. In this manner, the fraction collection line will be rendered essentially free of the last fraction component collected. The flush solvent may be provided by the HPLC system autosampler syringe and flush solvent port.

In most cases, the fractions collected, containing the compounds of interest, will require quantitation. "Quantitation" is defined here as the measurement of the concentration of the product of interest in the eluted fraction collected. Quantitation may be performed by several techniques. For example, NMR using suitable internal standards is generally the most accurate means of quantitating, but is also time consuming and difficult to implement without prior method development work. It is preferable that quantitation be performed rapidly and with minimal operator involvement, otherwise the efficiency of the present method will be compromised. Consequently, it is preferable to perform sample quantitation by HPLC with ELSD.

With respect to this detection technique, reference may be had to: Michel Lafosse, Claire Elfakir, Luc Morin-Allory, and Michel Dreux, "The Advantages of Evaporative Light Scattering Detection in Pharmaceutical Analysis by High Performance Liquid Chromatography and Supercritical Fluid Chromatography", JOURNAL OF HIGH RESOLUTION CHROMATOGRAPHY, Vol. 15, May 1992; Paul A. Asmus and John B. Landis, "Analysis of Steroids in Bulk Pharmaceuticals by Liquid Chromatography with Light-Scattering Detection", JOURNAL OF CHROMATOGRAPHY, 316, 461–472 (1984); Jeffrey A. Peterson and Donald S. Risley, "Validation of an HPLC Method for the Determination of Sodium in LY293111 Sodium, a Novel LTC₄ Receptor Antagonist, Using Evaporative Light Scattering Detection", JOURNAL OF LIQUID CHROMATOGRAPHY, 18(2), 331–338 (1995).

The quantitation may be performed on a sample having had the mobile phase stripped away and reconstituted, or alternatively, is performed on the same fraction following collection using an analytical HPLC equipped with an evaporative light scattering detector. Suitable evaporative light scattering detectors for quantitation include the Varex (Burtonsville, Md.) Model MK-III and the Sedex Models 55 and 65 detectors available from Sedere, Alfortville, France. In the latter case, the total sample volume needed for calculation of sample concentration could be determined by the system software as the product of the chromatographic eluent's volumetric flow rate and sample collection time.

By the term "preparative HPLC" and like terms is meant an HPLC system which is capable of producing high microgram, milligram, or gram sized product fractions. Thus, for purposes of the present application, the term "preparative" includes both preparative and semi-preparative columns, but does not apply to analytical columns, which provide fractions in the nanogram to low μg range. By the term "mechanically actuatable" pertaining to the switching valve is meant a valve whose different positions are selected by other than manual actuation, i.e., by computer selection. The actual mechanical actuation may be electric (i.e. a solenoid controlled valve), pneumatic (i.e. an air pressure controlled valve), hydraulic (a liquid pressure controlled valve), or any other equivalent means.

In the claims which follow, the individual steps need not necessarily be performed in the order listed in the claim, so long as the step or its equivalent is performed at some time. In like manner, multiple individual steps may be combined into a single step. The claims should be construed as facilitating the objects of the invention and like objects.

By the term "HPLC compatible detector" is meant a detector suitable for employment in an HPLC system which is capable of providing a detectable signal upon elution of a compound peak. A detector not capable of generating a signal under these conditions, i.e. a UV detector employing 205 nm radiation where the compound has substantially no absorbance at 205 nm, is not an HPLC compatible detector. Where component absorbance varies widely, it may be necessary to utilize more than one detector. A detector capable of detecting a desired component is not rendered an "incompatible" detector by its inability to detect a non-desired peak.

By the term "waste reservoir" is meant a destination suitable for collection of eluate not containing a sample of interest or which for whatever reason is not desired of saving. The waste reservoir in most cases will be a collection vessel of some type, for example, a flask, bottle, or jug. Similarly, by the term "compound reservoir" and like terms, is meant a container suitable for collection of desired samples. In most cases, since sample size will be relatively small, a vial, test tube, or other component suitable for use in standard autosampler or fraction collectors will be used. However, a flask, bottle, jug, etc. may be used as well, particularly if the purification is to be repeated many times.

Having now fully described the invention, it will be apparent to one of ordinary skill in the art that many changes and modifications can be made thereto without departing from the spirit or scope of the invention as set forth herein.

What is claimed is:

1. An automated method for the separation and purification of one or more compound(s) of interest from a mixture containing a plurality of components including said compound(s), comprising:

a) subjecting a first sample of said mixture to separation by high performance liquid chromatography forming a stream of eluate, differing portions of said stream of eluate containing said compound(s) separated from other portions of eluate not containing said compound (s), a concentration of each of said differing portions of eluate representable by a chromatogram having a plurality of peaks extending above a baseline, each of said peaks corresponding to at least one component of said mixture, said peaks individually assigned an identifier corresponding to the position of a peak relative to other peaks;

b) identifying which of said plurality of peaks correspond to compound(s) of interest;

c) storing said chromatogram in digital format;

d) selecting one or more peaks corresponding to compound(s) of interest for purification;

e) providing a semi-preparative or preparative HPLC system having an HPLC column, said semi-preparative or preparative HPLC system employing an HPLC compatible detector having an electrical output, said electrical output applied to an analog/digital converter to produce a digitized detector signal, and having a mechanically actuatable fluid switching valve capable of directing flow of eluate from said semi-preparative or preparative HPLC column from at least one waste reservoir to at least one compound reservoir;

f) selecting a threshold limit for said digitized detector signal such that excursions above said threshold limit will logically correspond to one or more compound peaks of said chromatogram;

g) injecting a sample into said semi-preparative or preparative HPLC system with said mechanically actuatable fluid switching valve in position such that eluate is directed to said waste reservoir;

h) comparing said digitized detector output to said threshold limit and identifying said compound peak(s);

i) upon sensing a desired compound peak, actuating said mechanically actuatable fluid switching valve to direct eluate into said compound reservoir to collect a compound-containing eluate, wherein said peak identifier and said threshold limit are digitally stored in a computer, said computer performing step h) and generating actuating signals as required by step i).

2. The method of claim 1 wherein following said step i), j) said mechanically actuatable fluid switching valve is actuated to direct said eluate to said waste reservoir.

3. The process of claim 2 wherein a plurality of compounds of interest are to be purified, further comprising repeating steps h) through j).

4. The process of claim 2 wherein said separation and purification is to be effected an n plurality of times on successive samples from the same set of heterogeneous or homogeneous mixtures, comprising repeating steps g) through j).

5. The method of claim 2 further comprising quantitating said compound-containing eluate.

6. The method of claim 5 wherein said quantitating is performed on said compound-containing eluate using HPLC employing an ELSD detector.

7. The method of claim 6 wherein said HPLC-compatible detector monitors the eluate of said preparative HPLC column as the eluate elutes from said column.

8. The method of claim 2 wherein following a conclusion of collecting a compound-containing eluate, a line providing for eluate flow between said mechanically actuatable fluid switching valve and said compound reservoir is flushed to substantially eliminate said compound from said line.

9. The method of claim 2 wherein said steps a) and b) are performed by HPLC/MS.

10. The process of claim 1 wherein said separation and purification is to be effected an n plurality of times on successive samples from the same mixture, comprising repeating steps g) through i).

11. The method of claim 1 further comprising quantitating said compound-containing eluate.

12. The method of claim 11 wherein said quantitating is performed on said compound-containing eluate using HPLC employing an HPLC compatible detector.

13. The method of claim 12 wherein said HPLC-compatible detector monitors the eluate of said semi-preparative or preparative HPLC column as the eluate elutes from said column.

14. The method of claim 1 wherein following a conclusion of collecting a compound-containing eluate, a line providing for eluate flow between said mechanically actuatable fluid switching valve and said compound reservoir is flushed to substantially eliminate said compound from said line.

15. The method of claim 1 wherein said steps a) and b) are performed by HPLC/MS.

* * * * *